(12) United States Patent
Kim et al.

(10) Patent No.: US 8,228,503 B2
(45) Date of Patent: Jul. 24, 2012

(54) APPARATUS FOR DETECTING PARTICLE

(75) Inventors: Taeg-Gyum Kim, Yongin-si (KR); Kwang-Ho Ji, Hwasung-si (KR)

(73) Assignee: Samsung Electro-Mechanics Co., Ltd., Gyunggi-do (KR)

( * ) Notice: Subject to any disclaimer, the term of this patent is extended or adjusted under 35 U.S.C. 154(b) by 57 days.

(21) Appl. No.: 12/857,974

(22) Filed: Aug. 17, 2010

(65) Prior Publication Data
US 2011/0242534 A1    Oct. 6, 2011

(30) Foreign Application Priority Data

Apr. 6, 2010  (KR) .................. 10-2010-0031282

(51) Int. Cl.
*G01N 21/00* (2006.01)
(52) U.S. Cl. ...................................... 356/337; 356/338
(58) Field of Classification Search ........... 356/337–343
See application file for complete search history.

(56) References Cited

U.S. PATENT DOCUMENTS

| | | | | |
|---|---|---|---|---|
| 5,739,902 | A * | 4/1998 | Gjelsnes et al. | 356/73 |
| 6,177,994 | B1 * | 1/2001 | Watson et al. | 356/343 |
| 6,970,246 | B2 * | 11/2005 | Hansen | 356/417 |
| 2008/0285032 | A1 * | 11/2008 | Ohkubo | 356/343 |

FOREIGN PATENT DOCUMENTS

JP     1990-038842    2/1990

OTHER PUBLICATIONS

Korean Office Action, w/ English translation thereof, issued in Korean Patent Application No. 10-2010-0031282, dated Mar. 12, 2012.

* cited by examiner

*Primary Examiner* — Tri T Ton
(74) *Attorney, Agent, or Firm* — McDermott Will & Emery LLP

(57) ABSTRACT

An apparatus for detecting a particle is disclosed. The apparatus for detecting a particle in a fluid in accordance with an embodiment of the present invention can include a first light source, which emits a first beam having a wavelength of a particular band toward the fluid, a second light source, which emits a second beam having a wavelength of a band that is different from that of the first beam, a first dichroic mirror, which is placed between the fluid and the first light source and allows the first beam to permeate and reflect the second beam toward the fluid, and a detecting unit, which detects a dispersed beam of the first beam and the second beam in the fluid. An embodiment of the invention can improve the reliability of detection by detecting a particle using a beam that has an optimal permeability according to the type of solution.

3 Claims, 3 Drawing Sheets

APPARATUS FOR DETECTING PARTICLE

CROSS-REFERENCE TO RELATED APPLICATIONS

This application claims the benefit of Korean Patent Application No. 10-2010-0031282, filed with the Korean Intellectual Property Office on Apr. 6, 2010, the disclosure of which is incorporated herein by reference in its entirety.

BACKGROUND

1. Technical Field

The present invention is related to an apparatus for detecting a particle.

2. Description of the Related Art

Foreign particles, both organic and inorganic, in a plating solution cause defective plating of a substrate in a process of fabricating a printed circuit board. These foreign particles are introduced from the outside and/or generated within the plating solution, that is, generated by the break-down and/or coagulation of a plating additive. If it were possible to detect the presence and the size of foreign particles in real time, it would be possible to preclude the cause of the foreign particles and substantially lower the defective plating of the substrate.

In a widely known method of detecting a foreign particle in a solution, laser is irradiated into the solution in a plating tank, and the light dispersed by the foreign particle is collected to detect the foreign particle from the signal of the collected light.

However, in case it is difficult to permeate the laser beam into the solution, the detection is ether impossible or unreliable. Especially, since plating solutions are highly concentrated, it is difficult to permeate the red light, which is commonly used in commercial particle detectors, into the solution, making it difficult to detect a foreign particle reliably.

Moreover, since the permeability of laser beam is different for each different type of plating solution, the apparatus for detecting a foreign particle needs to be changed when a different plating solution is used.

SUMMARY

The present invention provides an apparatus for detecting a particle that can reliably detect the particle in various solutions.

An aspect of the present invention provides an apparatus for detecting a particle in a fluid. The apparatus for detecting a particle in a fluid in accordance with an embodiment of the present invention can include a first light source, which emits a first beam having a wavelength of a particular band toward the fluid, a second light source, which emits a second beam having a wavelength of a band that is different from that of the first beam, a first dichroic mirror, which is placed between the fluid and the first light source and allows the first beam to permeate and reflect the second beam toward the fluid, and a detecting unit, which detects a dispersed beam of the first beam and the second beam in the fluid.

The apparatus for detecting a particle in a fluid in accordance with an embodiment of the present invention can also include an adjusting lens placed, which is between the first dichroic mirror and the fluid and adjusts the first beam and the second beam incident at the fluid.

The apparatus for detecting a particle in a fluid in accordance with an embodiment of the present invention can also include a shutter, which selectively blocks the first beam or the second beam.

The apparatus for detecting a particle in a fluid in accordance with an embodiment of the present invention can also include a third light source, which emits a third beam having a wavelength of a band that is different from those of the first beam and the second beam, and a second dichroic mirror, which reflects the second beam toward the first dichroic mirror and allows the third beam to permeate through so as to be directed to the first dichroic mirror. The first dichroic mirror can reflect the third beam toward the fluid.

Additional aspects and advantages of the present invention will be set forth in part in the description which follows, and in part will be obvious from the description, or may be learned by practice of the invention.

DETAILED DESCRIPTION

Figure 1:
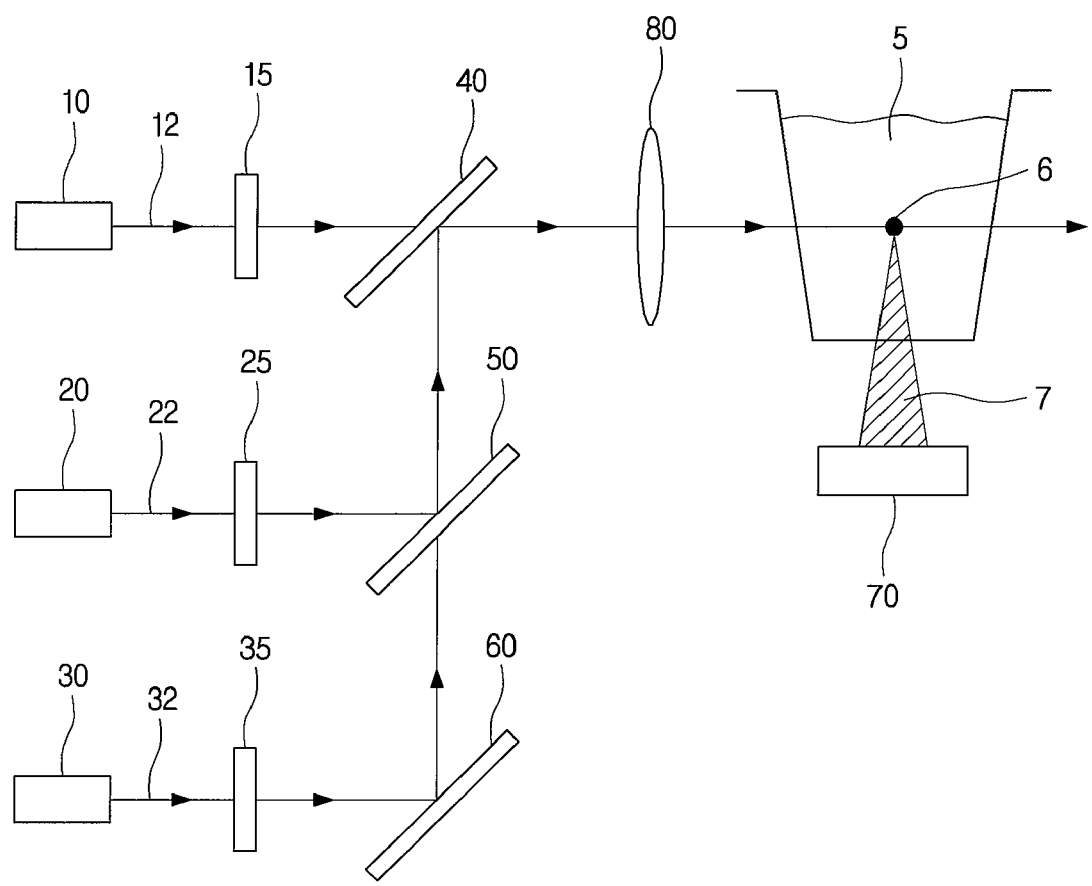
FIG. 1 shows an apparatus for detecting a particle in accordance with an embodiment of the present invention.

As the invention allows for various changes and numerous embodiments, a particular embodiment will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In the description of the present invention, certain detailed descriptions of related art are omitted when it is deemed that they may unnecessarily obscure the essence of the invention.

While such terms as "first" and "second," etc., may be used to describe various components, such components must not be limited to the above terms. The above terms are used only to distinguish one component from another. For example, a first component may be referred to as a second component without departing from the scope of rights of the present invention, and likewise a second component may be referred to as a first component. The term "and/or" encompasses both combinations of the plurality of related items disclosed and any item from among the plurality of related items disclosed.

The terms used in the present specification are merely used to describe particular embodiments, and are not intended to limit the present invention. An expression used in the singular encompasses the expression of the plural, unless it has a clearly different meaning in the context. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

An apparatus for detecting a particle according to a certain embodiment of the invention will be described below in more detail with reference to the accompanying drawings. Those components that are the same or are in correspondence are rendered the same reference numeral regardless of the figure number, and redundant descriptions are omitted.

FIG. 1 shows an apparatus for detecting a particle in accordance with an embodiment of the present invention.

The apparatus for detecting a particle in accordance with an embodiment of the present invention detects a particle 6 in a fluid 5 and includes a first light source 10, a second light source 20, a first dichroic mirror 40 and a detecting unit 70.

The first light source 10 and the second light source 20 emit a first beam 12 and a second beam 22, respectively, each of which has a wavelength in a different band. Here, each of the first beam 12 and the second beam 22 can have an optimal permeability for the fluid 5 being detected. In addition, in order for the first beam 12 and the second beam 22 to be directed to the fluid 5 being detected, the first light source 10 is disposed to be directed to the fluid 5 directly, and the second light source 20 is reflected by the first dichroic mirror 40, which will be described later, and directed to the fluid 5.

In the present embodiment, the first beam 12 is configured to have an optimal permeability in a plating solution used in electrolytic plating, and the second beam 22 is configured to have an optimal permeability in a plating solution used in electroless plating. Accordingly, the first beam 12 is used when the foreign particle is to be detected in a plating solution for electrolytic plating, and the second beam 22 is used when the foreign particle is to be detected in a plating solution for electroless plating.

Figure 3:
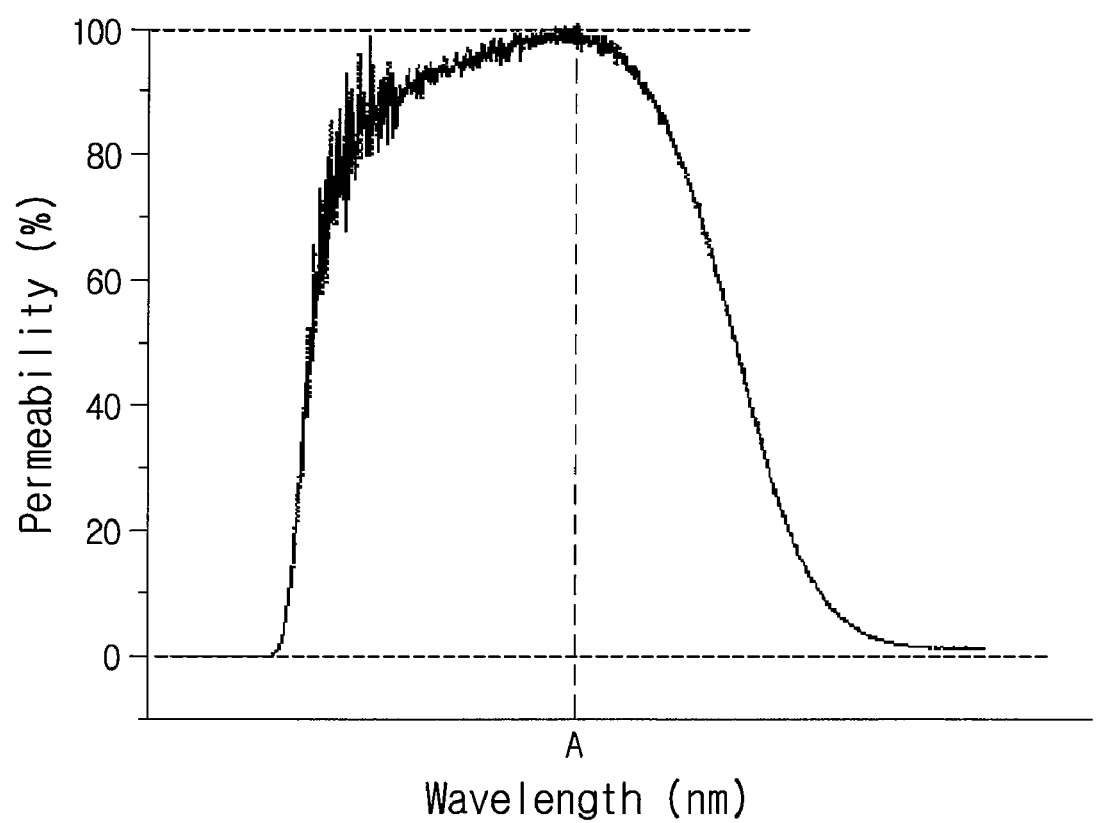
FIG. 3 is a graph illustrating the permeability of a plating solution used in electrolytic plating.

Specifically, since a beam with a wavelength of A has the highest permeability in a plating solution for electrolytic plating, as illustrated in FIG. 3, the first beam 12 is configured to have a wavelength in a particular band about the wavelength of A.

Therefore, the apparatus for detecting a particle in accordance with the present embodiment can improve the reliability of detecting the particle in a plating solution even though the type of plating solution, which is the fluid 5 being detected, is changed, by providing a beam having the optimal permeability for the changed plating solution. In other words, by using a beam having a high permeability for the plating solution, the probability and angular resolution of detecting the particle 6 can be improved.

The first dichroic mirror 40 is a part that controls the path of a beam such that both the first beam 12 and the second beam 22 can be directed to the fluid 5. Accordingly, a beam of a certain wavelength can be permeated while a beam of other wavelengths can be reflected.

Figure 2:
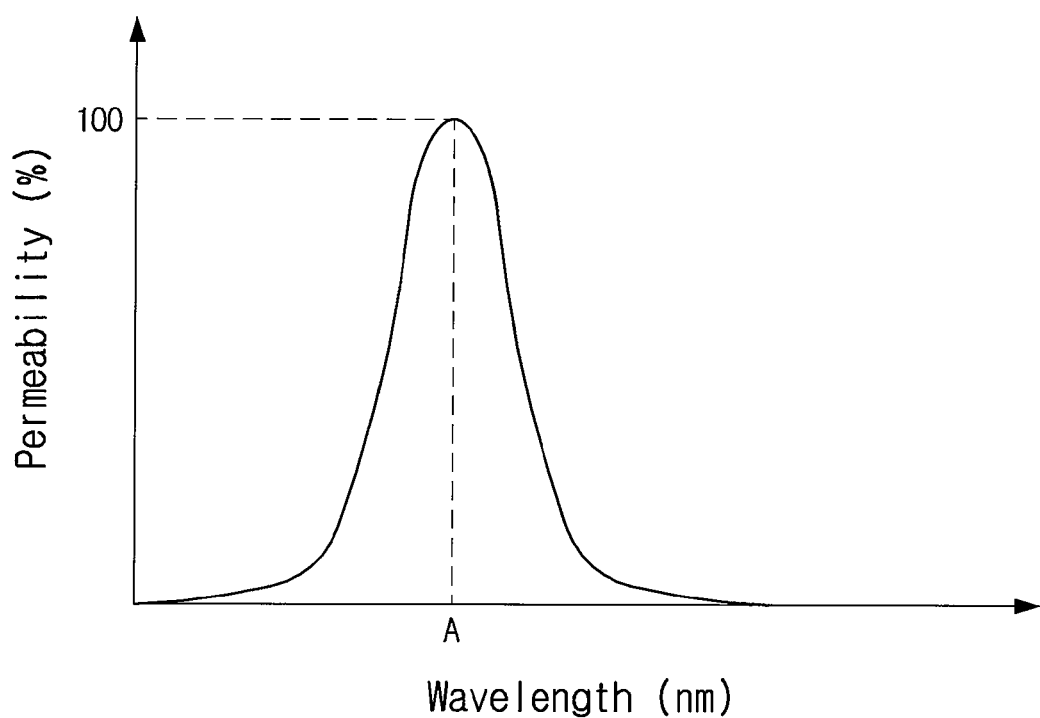
FIG. 2 is a graph illustrating the property of a first dichroic mirror in an apparatus for detecting a particle in accordance with an embodiment of the present invention.

FIG. 2 is a graph illustrating the property of the first dichroic mirror 40 in the apparatus for detecting a particle in accordance with an embodiment of the present invention.

As illustrated in FIG. 2, the first dichroic mirror 40 of the present embodiment is configured to allow the first beam 12 having the wavelength of A to permeate and the second beam 22 having the wavelength of a different band to reflect.

Accordingly, as illustrated in FIG. 1, the first dichroic mirror 40 is placed between the fluid 5 and the first light source 10 to allow the first beam 12, which is emitted toward the fluid 5, to reach the fluid 5. By being slanted on the path of the second beam 22, the first dichroic mirror 40 allows the second beam to reflect toward the fluid 5.

The apparatus for detecting a particle in accordance with the present embodiment can emit a plurality of beams through a single path. In addition, by controlling the first light source 10 and the second light source 20, the apparatus for detecting a particle in accordance with the present embodiment can selectively emit the first beam 12 and the second beam 22. Accordingly, even though the plating solution is changed, it is not required to change the apparatus for detecting a particle to a different apparatus, and it is possible to detect a particle in the changed plating solution by controlling the kind of light source.

Here, the apparatus for detecting a particle in accordance with the present embodiment can additionally include shutters 15 and 25 that selectively block the first beam 12 or the second beam 22, in order to make the control of the first beam 12 and the second beam 22 easier. The shutters 15 and 25 can block the first beam 12 or the second beam 22 or allow the first beam 12 or the second beam 22 to pass through.

In the present embodiment, the shutters 15 and 25 are placed in front of the first light source 10 and the second light source 20, respectively, thereby allowing the first beam 12 and the second beam 22 to be selectively incident at the fluid 5.

The detecting unit 70 detects how much the first beam 12 or the second beam 22 permeated into the fluid 5 is dispersed by the particle 6 in the fluid 5. That is, by detecting a dispersed beam 7, the presence of the particle 6 and the size of the particle 6 in the fluid 5 are detected.

Here, the signal strength of the dispersed beam 7 is related to the size of the particle 6. Thus, if a beam permeated into the fluid 5 is not properly permeated and absorbed by the plating solution, a detection error can occur, and the relation between the signal strength of the dispersed beam and the size of the particle becomes unreliable. To prevent this, the present embodiment selects a beam that has the optimal permeability for a particular plating solution in order to secure the reliability of detection, as described earlier.

Moreover, the apparatus for detecting a particle in accordance with the present embodiment can further include an adjusting lens 80 that adjusts the first beam 12 and the second beam 22 that are incident at the fluid 5, so as to facilitate the formation of the dispersed beam 7. The adjusting lens 80 is placed between the first dichroic mirror 40 and the fluid 5 and allows the first beam 12 and the second beam 22 passing through the adjusting lens 80 to converge or diverge so as to adjust the first beam 12 and the second beam 22 to a form that is easier for detection.

The apparatus for detecting a particle in accordance with an embodiment of the present invention can additionally include a third light source 30 or a plurality of light sources, in addition to the first light source 10 and the second light source 20. Specifically, as illustrated in FIG. 1, the apparatus for detecting a particle in accordance with an embodiment of the present invention can additionally include the third light source 30, which emits a third beam 32 having a wavelength of a band that is different from those of the first beam 12 and the second beam 22, and a second dichroic mirror 50, which reflects the second beam 22 toward the first dichroic mirror 40 and allows the third beam 32 to permeate toward the first dichroic mirror 40. Here, the first dichroic mirror 40 is configured to reflect the third beam 32 together with the second beam 22.

Accordingly, the first beam 12 permeates through the first dichroic mirror 40 and is directed toward the fluid 5 directly, and the second beam 22 is reflected by the second dichroic mirror 50 and then reflected by the first dichroic mirror 40 to be directed toward the fluid 5. Moreover, the third beam 32 permeates through the second dichroic mirror 50 and then is reflected by the first dichroic mirror 40 to be directed toward the fluid 5. Here, the third beam 32 can be guided by a reflective mirror 60 so as to permeate through the second dichroic mirror 50 and be directed to the first dichroic mirror 40. In addition, the third beam 32 can be also blocked or allowed to pass through by a shutter 35.

Therefore, by selectively using a plurality of light sources in one apparatus for detecting a particle, an optimal beam for a particular particle can be used to improve the reliability of detection.

The present invention can improve the reliability of detection by detecting the particle using a beam that has an optimal permeability according to the type of solution.

Moreover, it is possible to detect the particle in various solutions, without changing the apparatus.

While the spirit of the invention has been described in detail with reference to a certain embodiment, the embodiment is for illustrative purposes only and shall not limit the invention. It is to be appreciated that those skilled in the art can change or modify the embodiment without departing from the scope and spirit of the invention.

As such, many embodiments other than that set forth above can be found in the appended claims.

What is claimed is:

1. An apparatus for detecting a particle in a fluid, the apparatus comprising:
    a first light source configured to emit a first beam toward the fluid, the first beam having a wavelength of a particular band;
    a second light source configured to emit a second beam having a wavelength of a band that is different from that of the first beam;
    a third light source configured to emit a third beam having a wavelength of a band that is different from those of the first beam and the second beam;
    a first dichroic mirror placed between the fluid and the first light source, the first dichroic mirror configured to allow the first beam to permeate through so as to be directed to the fluid and reflect the second beam and the third beam toward the fluid;
    a second dichroic mirror placed among the first dichroic mirror, the second light source and the third light source, the second dichroic mirror configured to reflect the second beam toward the first dichroic mirror and allow the third beam to permeate through so as to be directed to the first dichroic mirror; and
    a detecting unit configured to detect a dispersed beam of the first beam and the second beam and the third beam in the fluid.

2. The apparatus of claim 1, further comprising:
an adjusting lens placed between the first dichroic mirror and the fluid, the adjusting lens being configured to adjust the first beam and the second beam incident at the fluid.

3. The apparatus of claim 1, further comprising:
a shutter configured to selectively block the first beam or the second beam.

* * * * *